(12) United States Patent
Tan

(10) Patent No.: US 8,575,330 B2
(45) Date of Patent: Nov. 5, 2013

(54) MICRORNA-BASED SHORT HAIRPIN RNA FOR GENE KNOCKDOWN OF NR1 SUBUNIT OF N-METHYL-D-ASPARTATE RECEPTOR AND ITS APPLICATION ON PHARMACEUTICS

(75) Inventor: Ping-Heng Tan, Kaohsiung (TW)

(73) Assignee: I-Shou University, Kaohsiung (TW)

( * ) Notice: Subject to any disclaimer, the term of this patent is extended or adjusted under 35 U.S.C. 154(b) by 0 days.

(21) Appl. No.: 13/545,687

(22) Filed: Jul. 10, 2012

(65) Prior Publication Data
US 2013/0225653 A1 Aug. 29, 2013

(30) Foreign Application Priority Data
Feb. 23, 2012 (TW) .............................. 101106072 A

(51) Int. Cl.
*C07H 21/04* (2006.01)
(52) U.S. Cl.
USPC ......... 536/24.5; 536/24.31; 536/24.1; 514/44
(58) Field of Classification Search
None
See application file for complete search history.

(56) References Cited

U.S. PATENT DOCUMENTS

| 7,687,080 | B2 * | 3/2010 | Wolicki | ........................ 424/725 |
| 2008/0294089 | A1 * | 11/2008 | Hardy | ............................. 604/22 |
| 2011/0263676 | A1 | 10/2011 | Tan | |

OTHER PUBLICATIONS

Garraway et al. (The Journal of Pharmacology and Experimental Therapeutics, 2007, 322, 982-988).*
Miskevich et al. (Journal of Neuroscience Methods 152, 2006:65-73).*
Tan, et al., "Gene Knockdown of the N-Methyl-D-Aspartate Receptor NR1 Subunit with Subcutaneous Small Interfering RNA Reduces Inflammation-induced Nociception in Rats", Anesthesiology 2010; 112, pp. 1482-1493.
Tan, et al., "RNA interference-mediated gene silence of the NR1 subunit of the NMDA receptor by subcutaneous injection of vector-encoding short hairpin RNA reduces formalin-induced nociception in the rat", PAIN, 2011, pp. 1-9.
Stegmeir, et al., "A lentiviral microRNA-based system for single-copy polymerase II-regulated RNA interference in mammalian cells", PNAS, vol. 102, No. 37, Sep. 13, 2005, pp. 13212-13217.

* cited by examiner

*Primary Examiner* — Kimberly Chong
(74) *Attorney, Agent, or Firm* — Muncy, Geissler, Olds & Lowe, PLLC

(57) ABSTRACT

The present invention relates to a microRNA-based short hairpin RNA for gene silencing the genetic expression of NR1 subunit of N-methyl-D-aspartate receptor comprises a single strand RNA fragment comprising a first fragment, a second fragment and a connecting fragment, wherein the first fragment and the second fragment are complementary to each other, and are spaced and connected by the connecting fragment, with the connecting fragment being randomly arranged nucleotides, with the first fragment having a Drosha recognized cleavage site, a silencing site and a Dicer recognized cleavage site, with the Drosha recognized cleavage site and the Dicer recognized cleavage site being spaced and connected by the silencing site, with the silencing site encoding homologous nucleotides corresponding to NR1 subunit of subcutaneous N-methyl-D-aspartate receptor.

14 Claims, 7 Drawing Sheets

SEQUENCE LISTING

```
<160> NUMBER OF SEQ ID NOS: 19

<210> SEQ ID NO 1
<211> LENGTH: 97
<212> TYPE: DNA
<213> ORGANISM: Artificial Sequence
<220> FEATURE:
<223> OTHER INFORMATION: Synthetic oligonucleotide

<400> SEQUENCE: 1
tgctgttgac agtgagcgac gggtaaacaa cagcaacaaa tagtgaagcc acagatgtat      60
ttgttgctgt tgtttacccg ctgcctactg cctcgga                              97

<210> SEQ ID NO 2
<211> LENGTH: 96
<212> TYPE: DNA
<213> ORGANISM: Artificial Sequence
<220> FEATURE:
<223> OTHER INFORMATION: Synthetic oligonucleotide
```

<400> SEQUENCE: 2
tgctgttgac agtgagcgac agactaaaga tagtgacaaa tagtgaagcc acagatgtat    60
ttgtactgtc tttagtctgc tgcctactgc ctcgga                              96

<210> SEQ ID NO 3
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 3
ggguaaacaa cagcaacaa                                                 19

<210> SEQ ID NO 4
<211> LENGTH: 19
<212> TYPE: RNA
<213> ORGANISM: Artificial Sequence
<220> FEATURE:
<223> OTHER INFORMATION: Synthetic oligonucleotides

<400> SEQUENCE: 4
agacuaaaga uagugacaa                                                 19

<210> SEQ ID NO 5
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 5
auagugaagc cacagaugua u                                              21

<210> SEQ ID NO 6
<211> LENGTH: 97
<212> TYPE: RNA
<213> ORGANISM: Artificial Sequence
<220> FEATURE:
<223> OTHER INFORMATION: Synthetic oligonucleotide

<400> SEQUENCE: 6
ugcuguugac agugagcgac ggguaaacaa cagcaacaaa uagugaagcc acagauguau    60
uuguugcugu uguuacccg cugccuacug ccucgga                              97

<210> SEQ ID NO 7
<211> LENGTH: 96
<212> TYPE: RNA
<213> ORGANISM: Artificial Sequence
<220> FEATURE:
<223> OTHER INFORMATION: Synthetic oligonucleotide

<400> SEQUENCE: 7
ugcuguugac agugagcgac agacuaaaga uagugacaaa uagugaagcc acagauguau    60
uuguacuguc uuuagucugc ugccuacugc cucgga                              96

<210> SEQ ID NO 8
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 8
gcgactcccg cagcaat                                              17

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
cccctgccat gttctcaaaa                                           20

<210> SEQ ID NO 10
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 10
tccactcaag gaatcttgtg agatat                                    26

<210> SEQ ID NO 11
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 11
acttgcccat gtgtatttat ttgttt                                    26

<210> SEQ ID NO 12
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 12
aaccctcgtg gccgaca                                              17

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
ggtggacaga tgcgggaa                                             18

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
ggcccagctt ttgaccttag t                                         21

<210> SEQ ID NO 15
<211> LENGTH: 19
<212> TYPE: DNA
<213> ORGANISM: Artificial Sequence

```
<220> FEATURE:
<223> OTHER INFORMATION: Synthetic oligonucleotide

<400> SEQUENCE: 15
cctgtgacca ccgcaagag                                               19

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
agggtttctg cattgcccca tt                                           22

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
tcaccaatca tgccattcca                                              20

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
cttggctgtt tgccccatt                                               19

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
cgtgacagta gctgcggttc c                                            21
```

MICRORNA-BASED SHORT HAIRPIN RNA FOR GENE KNOCKDOWN OF NR1 SUBUNIT OF N-METHYL-D-ASPARTATE RECEPTOR AND ITS APPLICATION ON PHARMACEUTICS

BACKGROUND OF THE INVENTION

1. Field of the Invention

The present invention relates to a microRNA-based short hairpin RNA, and a medicament comprising the said microRNA-based short hairpin RNA, particularly to a microRNA-based short hairpin RNA for silencing NR1 subunit of N-methyl-D-aspartate receptor, and an analgesic drug comprising the said microRNA-based short hairpin RNA.

2. Description of the Related Art

RNA interference refers to a phenomenon of post-transcriptional gene silencing being mediated by small double-stranded RNAs (also known as small interfering RNAs or siRNAs) that comprises endogenously encoded RNA to guide ribonucleoprotein complex, such as RNA induced silencing complex (RISA), to target message RNA (mRNA). The RNA interference is first discovered in 1990s in plants, the silencing mechanism thereof refers to exotic double-strand RNAs in cells being processed by Dicer and generating a plurality of siRNAs, with those siRNAs being self-unwound, targeting to particular messenger RNAs, further conducting RNA-induced silencing complex (RISC) to degrade the particular messenger RNAs, and finally resulting in post-transcriptional gene silencing on the said particular messenger RNAs.

In conventional arts, a siRNA, comprising 21 ribonucleic acids, has been developed, as reference to US publishing No. 2011/0263676 entitled "A SMALL INTERFERING RNA FOR GENE KNOCKDOWN OF THE SUBCUTANEOUS N-METHYL-D-ASPARTATE RECEPTOR NR1 SUBUNIT, AND IT'S APPLICATION ON PHARMACEUTICS," to achieve analgesic effects without leading to any side effects, such as nausea, lethargy, faint and motor un-coordination, that cause by conventional NMDA receptor antagonists (e.g. ketamine). By delivering the said siRNA to affected parts through subcutaneously injection, a temporary RNA interfering on NR1 subunit of N-methyl-D-aspartate receptor in hypoderm is conducted, so as to achieve antinociceptive effects on the affected parts.

However, due to the instability of the said siRNA, only a small amount of the said siRNA can truly affect on the affected parts, and therefore, a high dosage and a pharmaceutical acceptable carrier is needed to effectively deliver the said siRNA into nucleus for achieving NR1 silencing and analgesic. Also, the silencing effect of the said siRNA only last for 7 days, with the analgesic efficiency thereof decreasing by days after 7 days. Accordingly, a frequently injection is necessary if a long-term analgesic treatment is requested.

For improving the above-identified disadvantages of the said siRNA, a conventional analgesic is developed, as reference to U.S. application Ser. No. 13/027,742 entitled "A SHORT HAIRPIN RNA FOR GENE KNOCKDOWN OF NR1 SUBUNIT OF THE N-METHYL-D-ASPARTATE RECEPTOR AND ITS APPLICATION ON PHARMACEUTICS," and comprises a short hairpin RNA encoded in a pSilencer vector, being stable and easy to manufacture. The said short hairpin RNA has 45-65 nucleotides comprising a first fragment, a second fragment and a connection fragment, with the first fragment having homologous nucleotides among NR1 subunit of NMDA receptor, with the second fragment having complementary sequence to the first fragment, and with connecting fragment being 3-23 randomly arranged nucleotides. After delivering the conventional analgesic to affected parts, the said short hairpin RNA are transcribed by RNA polymerase III in cells, self-folded into a hairpin structure, and processed by endogenous nucleases to generate short double stranded RNAs, conducting a destruction of NR1 subunit of NMDA receptor medicated by RISC to achieve antinociception.

Although the said shRNA show lasting silencing effect (with duration of more than 14 days) on NR1 subunit of NMDA receptor in comparison with the said siRNA, it is poor in achieving immediately analgesic effect due to the late response of the said shRNA, with the antinociceptive effect thereof only presenting at least 7 days after cell-delivering. Therefore, the shRNA is failed to relieve acute pain. Furthermore, a dramatic dosage of a pharmaceutical acceptable carrier is needed for the said shRNA to reach a high delivering efficiency, and thus that the cost of the conventional analgesic in commercialization is high.

In 2005, Stegmeier et. al., have published a shRNA expression system (A Lentiviral microRNA-based System for Single-Copy Polymerase II-regulated RNA interference in mammalian cells. PNAS 102:13212-13217), to facilitate the tracking of shRNA production in cells, by providing a vector pPRIME to transcribe shRNAs under controls of RNA polymerase II and RNA polymerase III. The vector pPRIME provides sufficient penetrance for the use of encoded shRNAs. However, Stegmeier et. al. provides less information on practical uses of the said vector pPRIME and encoded shRNAs, especially in pharmaceutics.

Hence, it is necessary to improve the above-identified disadvantages and issues, and to provide an alternative strategy for achieving fast and lasting gene silencing on NR1 subunit of NMDA receptor, finally to accomplish fast and long-lasting antinociceptive effects and to put to use in pharmaceutics industry.

SUMMARY OF THE INVENTION

The primary objective of this invention is to provide a microRNA-based short hairpin RNA for gene silencing NR1 subunit of N-methyl-D-aspartate receptor, which provides fast and long-lasting silencing effect on the NR1 subunit of NMDA receptor.

Another objective of this invention is to provide an analgesic for skin inflammation pain, which is frugal in cost but is apt to provide fast and long-lasting analgesic effects on affected parts.

A microRNA-based short hairpin RNA for gene silencing the genetic expression of NR1 subunit of N-methyl-D-aspartate receptor comprises a single strand RNA fragment comprising a first fragment, a second fragment and a connecting fragment, wherein the first fragment and the second fragment are complementary to each other, and are spaced and connected by the connecting fragment, with the connecting fragment being randomly arranged nucleotides, with the first fragment having a Drosha recognized cleavage site, a silencing site and a Dicer recognized cleavage site, with the Drosha recognized cleavage site and the Dicer recognized cleavage site being spaced and connected by the silencing site, with the silencing site encoding homologous nucleotides corresponding to NR1 subunit of N-methyl-D-aspartate receptor.

The present invention relates to the said microRNA-based short hairpin RNA, wherein the silencing site comprises a sequence as set forth in SEQ ID No: 3 or 4.

The present invention relates to the said microRNA-based short hairpin RNA, wherein the connecting fragment comprises more than 10 nucleotides.

The present invention relates to the said microRNA-based short hairpin RNA, wherein the microRNA-based short hairpin RNA comprises a sequence as set forth in SEQ ID No: 6 or 7.

An analgesic drug for skin inflammation pain comprises a microRNA-based short hairpin RNA as defined in claim 1; and at least one pharmaceutical acceptable vehicle for the microRNA-based short hairpin RNA.

The present invention relates to the said analgesic drug, wherein the microRNA-based short hairpin RNA comprises a sequence as set forth in SEQ ID No: 6 or 7.

The present invention relates to the said analgesic drug, wherein the at least one pharmaceutical acceptable vehicle is polyethyleneimine.

The present invention relates to the said analgesic drug, wherein the microRNA-based short hairpin RNA is encoded by a pGIPZ vector.

The present invention relates to the said analgesic drug, wherein the dosage of the microRNA-based short hairpin RNA is 1 μg to 10 μg, being delivered every 7 days.

The present invention relates to the said analgesic drug, wherein the ratio of microRNA-based short hairpin RNA to the at least one acceptable vehicle is 5 μg: 1 μL.

Further scope of the applicability of the present invention will become apparent from the detailed description given hereinafter. However, it should be understood that the detailed description and specific examples, while indicating preferable embodiments of the invention, are given by way of illustration only, since various will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein.

In the various figures of the drawings, the same numerals designate the same or similar parts.

DETAILED DESCRIPTION OF THE INVENTION

The present invention provides a microRNA-based short hairpin RNAs encoding homologous nucleotides of a NR1 subunit of N-methyl-D-aspartate receptor, which targets to the NR1 subunit of N-methyl-D-aspartate receptor, interferes with the post-transcription the said NR1 subunit, and achieves fast and long-lasting antinociception mediated by silencing NR1 subunit.

Figure 1:
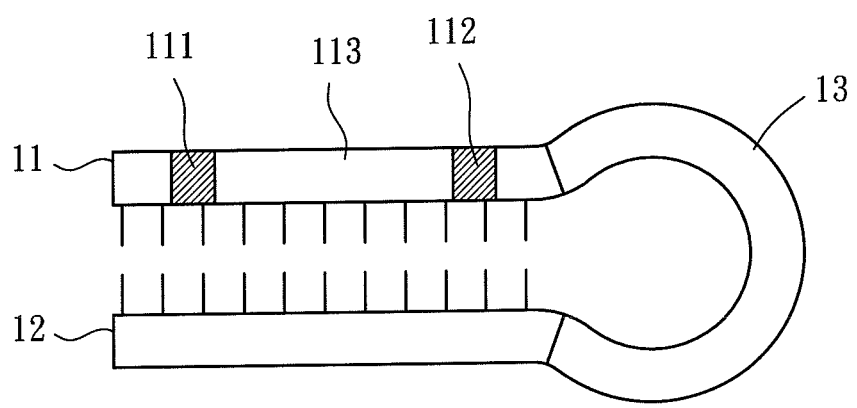
FIG. 1 is a diagram illustrating the structure of the microRNA-based short hairpin RNA of the present invention.

Referring to FIG. 1, the microRNA-based short hairpin RNA of the present invention comprises a single strand RNA fragment comprising a first fragment 11, a second fragment 12 and a connecting fragment 13, wherein the first fragment 11 and the second fragment 12 are complementary to each other, being spaced and connected by the connecting fragment 13. The connecting fragment 13 comprises randomly arranged nucleotides, preferably comprising more than 10 bases, and more preferably comprising 10-30 bases to properly space between the first fragment 11 and the second fragment 12. The first fragment has a Drosha recognized cleavage site 111, a Dicer recognized cleavage site 112, and a silencing site 113 sandwiched between the Drosha recognized cleavage site 111 and the Dicer recognized cleavage site 112, with the silencing site 113 encoding homologous nucleotides of the NR1 subunit of N-methyl-D-aspartate receptor.

When subcutaneously deliver the microRNA-based short hairpin RNA of the present invention into cells, the microRNA-based short hairpin RNA is transcribed as a long primary transcript (pri-microRNA-based short hairpin RNA) in a stem-loop structure that will further be recognized and trimmed both by RNase III enzyme Drosha and Dicer at the Drosha recognized cleavage site 111 and the Dicer recognized cleavage site 112 respectively, to obtain a small double-stranded RNA comprising the silencing site 113. Precisely, the pri-microRNA-based short hairpin RNA comprises over 70 nucleotides and has an internal loop which is recognized and trimmed by the RNase III enzyme Drosha at first, to obtain a pre-microRNA-based short hairpin RNA in a stem-loop form either. Then, the pre-microRNA-based short hairpin RNA is transported to cytoplasm and subjected to second trimming, with Dicer binding to the pre-microRNA-based short hairpin RNA, cleaving approximately 22 nucleotides away, followed by removing the loop and leaving a 2-nucleotide 3' overhang, to generate the small double-stranded RNA comprising silencing site 113 (including around 22 nucleotides). The small double-stranded RNA is apt to target to the NR1 subunit of N-methyl-D-aspartate receptor and to conduct gene silencing on the NR1 subunit, so as to turn down inflammatory pain and nociception mediated by the N-methyl-D-aspartate receptor.

In a preferable embodiment of the present invention, two microRNA-based short hairpin RNAs, NR1-1 and NR1-2, are designed and comprise sequences as set forth in NO. 1 or 2 individually, for specifically and rapidly targeting to the NR1 subunit of subcutaneous N-methyl-D-aspartate receptor and conducting gene silencing on the NR1 subunit. In precisely, the silencing site 113 of the two microRNA-based short hairpin RNAs comprise homologous RNA sequence to rat's NR1 subunit of NMDA receptor (referenced to NM017010 of Genebank of NCBI), as being set forth in SEQ ID NO. 3 and 4. Also, the connected fragments 13 of the two microRNA-based short hairpin RNAs comprise 21 bases as set forth in SEQ ID NO. 5.

The microRNA-based short hairpin RNA of the present invention can be manufactured by artificial synthesizing or being expressed with a vector. Preferably, the two microRNA-based short hairpin RNAs of the preferable embodiment of the present invention are but not limit to be encoded in a pGIPZ vector individually (Expression Arrest™ GIPZ lentiviral shRNAmir, Open Biosystems, cat no. RHS449) to obtain pGIPZ-NR1-1 and pGIPZ-NR1-2. The pGIPZ vector comprises CMV promoter and pol II promoter that is recognized by RNA polymerase II, and is capable of fast transcribing the encoded sequence thereof.

When subcutaneously delivering the pGIPZ-NR1-1 or pGIPZ-NR1-2 to hypoderm, the microRNA-based short hairpin RNAs, NR1-1 and NR1-2 as set forth in SEQ ID NO. 1 and 2 individually, are transcribed to pri-microRNA-based short hairpin RNA in a stem-loop structure and comprising sequences set forth in SEQ ID NO. 6 and 7. Next, the pri-microRNA-based short hairpin RNAs will be processed by RNase III enzyme Drosha and Dicer to generate small double-stranded RNAs, namely NR1-1 miRNA and NR1-2 miRNA that comprise sequences set forth in SEQ ID NO. 3 and 4 respectively. Accordingly, the small double-stranded RNAs, NR1-1 miRNA and NR1-2 miRNA, are apt to conduct post-transcriptional gene silencing on the NR1 subunit of subcutaneous NMDA receptor, and therefore, the NR1 subunit mediated inflammatory pain and nociception will be temporarily turned off either.

In the next paragraphs, for evidencing the silencing effects of the microRNA-based short hairpin RNA of the present invention, model animals, such as formalin-induced Sprangue-Dawley rats, are prepared to demonstrate the pain response and the post-transcriptional gene silencing of the NR1 in living organisms.

Sprangue-Dawley rats (SD rats), with 250 g to 350 g in weight, are prepared and housed at a standard laboratory environment for undergoing a serial of formalin-trials including trials of (A) microRNA-based short hairpin RNA; (B) dose-effect; and (C) time course. In the formalin-trials, the pGIPZ-NR1-1 or pGIPZ-NR1-2 of the present invention are subcutaneously injected to the SD rats with an acceptable vehicle under various conditions, and the flinch responses and NR1 expressions of the SD rats in each trial are monitored and summarized below.

Trial of (A) microRNA-Based Short Hairpin RNA:

With reference to Table 1, the SD rats are randomly assigned to four groups including (A1) vehicle group; (A2) saline group; (A3) pGIPZ-NR1-1 group; and (A4) pGIPZ-NR1-2 group, with each group having six rats respectively. The first injection is administered three days before the formalin injection (known as the second injection), by subcutaneously injecting 2 μL polyethyleneimine (PEI), 100 μL saline and 5 μg pGIPZ-NR1-1 and 5 μg pGIPZ-NR1-2 respectively in one paw of rats in (A1) to (A4) groups. The second injection is performed on the same paw of rats, with 1% formalin. Then, a flinching test and tissue dissection are carried out right after the second injection, for immediately analyzing rats' pain response and NR1 expression by real-time polymerase chain reaction (PCR). In the present trial, 5 μg of the pGIPZ-NR1-1 or pGIPZ-NR1-2 are mixed with 1 μL PEI (Fermentas Inc. Glen; Burnie) and further adjusted to 100 μl by 5% dextrose solution for convenient injecting.

TABLE 1

Groups Assignment in the Trial of (A) MicroRNA-Based Short Hairpin RNA

| groups | First injection | | Second injection | |
|---|---|---|---|---|
| | agents | dose | agents | dose |
| A1 | polyethyleneimine | 2 μL | 1% formalin | 50 μL |
| A2 | saline | 100 μL | 1% formalin | 50 μL |
| A3 | pGIPZ-NR1-1 | 5 μg | 1% formalin | 50 μL |
| A4 | pGIPZ-NR1-2 | 5 μg | 1% formalin | 50 μL |

Figure 2:
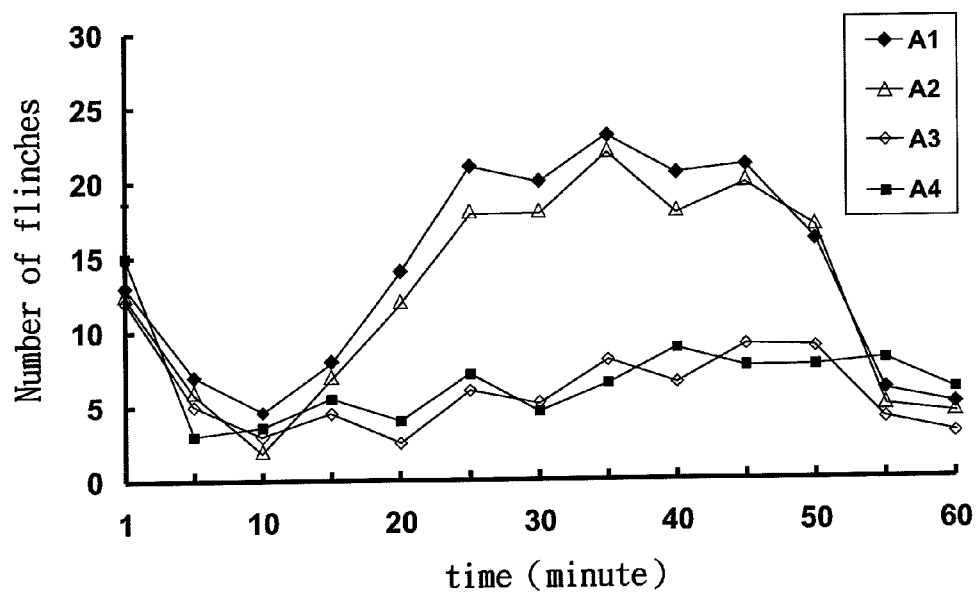
FIG. 2 is a line chart illustrating data of flinch responses in rats on formalin-induced nociception.

Referring to FIG. 2, the formalin-induced flinching responses in the SD rats of the groups (A1) to (A4) are shown, wherein two phases of nociceptive behavior, including acute phase and tonic phase, can be clearly observed on the SD rats after the second injection. As it is indicated in curves (A1) to (A4), the flinching behaviors of the acute phase begin immediately after the second injection (with 1% formalin) and last for three to five minutes. On the other hand, the flinching behaviors of the tonic phase begin at about twentieth minutes after the second injection and last for twenty to forty minutes. In comparison, the curve (A3) and (A4) points out that the flinching behaviors both in the acute phase and the tonic phase on the SD rats of the groups (A3) and (A4) are significantly minor among others. It is suggested that the SD rats had the pGIPZ-NR1-1 or the pGIPZ-NR1-2 injection show mild pain response to formalin-induced nociception.

Next, to examine the silencing effects of the pGIPZ-NR1-1 and the pGIPZ-NR1-2 of the present invention, total RNA samples of the SD rats of the four groups are collected from skin tissues and purified by using a total RNA mini kit (Geneaid Biotech Ltd; Sijhih City). The total RNA samples of the SD rats are further reverse-transcribed by using a DNA reverse transcription kit (Applied Biosystems Inc; Foster City) and analyzed by ABI prism 7500 sequence detection system (Applied Biosystems Inc; Foster City), for determining the expressed levels of NR1 in rats via real time PCR. In the present trial, specific primer pairs, NR1 comprising sequences as set forth in SEQ ID NO: 8 and 9, are designed and used in the real time PCR program for detecting the mRNA expression of the NR1 subunit in the SD rats of the four groups.

Figure 3:
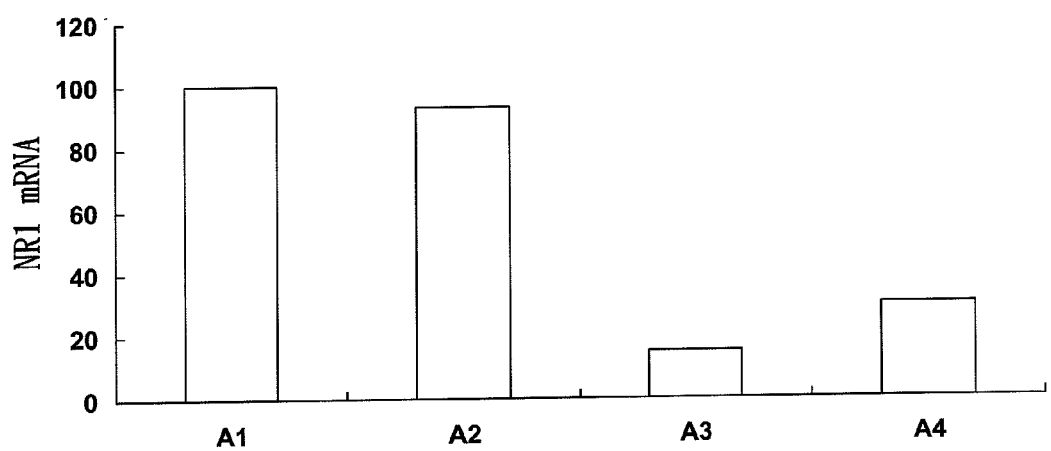
FIG. 3 is a bar chart showing mRNA expression of NR1 in rats after subcutaneous injection of the microRNA-based short hairpin RNA of the present invention.

Referring to FIG. 3, the mRNA expressions of NR1 subunit on rats in each group are shown, wherein the NR1 expressions of the groups (A3) and (A4), especially of the groups (A3), are significantly lower than that of the groups (A1) and (A2). In the present trial, the expressed level of NR1 of the group (A1) is defined as 100% and thus that, the SD rats in the groups (A2) to (A4) only have 93%, 15%, and 30% of NR1 expression respectively in comparison with the group (A1). It is noted that the mRNA expression of NR1 subunit in the SD rats is dramatically suppressed by pGIPZ-NR1-1 and the pGIPZ-NR1-2 of the present invention.

It is believed that the microRANs NR1-1 and NR1-2 encoded in the pGIPZ-NR1-1 and the pGIPZ-NR1-2 are fast transcribed to pri-microRNA-based short hairpin RNAs and processed by RNase III enzyme Drosha and Dicer, finally to obtain the small double-stranded RNAs, double-stranded RNAs NR1-1 and NR1-2 in rats. With the double-stranded RNAs NR1-1 and NR1-2 specifically target to NR1 subunit of N-methyl-D-aspartate receptor, conduct post-transcriptional gene silencing on the NR1 subunit in rats, and finally turn down the pain responses mediated by the NR1 subunit.

(B) Trial of Dose-Effect

With reference to Table 2, the SD rats were randomly assigned to seven groups including (B1) vehicle group; (B2) saline group; (B3) pGIPZ-NS-NR1-1 group; (B4) contralateral groups; (B5) 1 μg pGIPZ-NR1-1; (B6) 5 μg pGIPZ-NR1-1 group; and (B7) 10 μg pGIPZ-NR1-1 groups, with subcutaneous injecting 2 μl PEI, 100 saline, 5 μg pGIPZ-NS-NR1-1, and 5 μg, 1 μg, 5 μg and 10 μg pGIPZ-NR1-1 respectively. The pGIPZ-NS-NR1-1 comprises non-silencing NR1 microRNA-based short hairpin RNA as set forth in SEQ ID NO. 18, and which will not lead to post-transcriptional gene silencing on the NR1-1 subunit. Similar to the trial of (A) microRNA-based short hairpin RNA, the first injection is administered on one paw of the SD rats of each group three days prior than the second injection that gives formalin to the same paw of the SD rats in groups (B1) to (B3) and (B5) to (B7), but on contralateral paw of the SD rats in group (B4). Also, the flinching test and tissue dissection are also performed on the SD rats of the seven groups after the second injection, for immediately analyzing rats' pain response and NR1 expression.

TABLE 2

Groups Assignment in the Trial of (B) Dose-Effect

| groups | First injection | | Second injection | |
|---|---|---|---|---|
| | agents | dosage | agents | dosage |
| B1 | PEI | 2 μL | 1% formalin | 50 μL |
| B2 | saline | 100 μL | 1% formalin | 50 μL |
| B3 | pGIPZ-NS-NR1-1 | 5 μg | 1% formalin | 50 μL |
| B4 | pGIPZ-NR1-1 | 5 μg | 1% formalin$^a$ | 50 μL |
| B5 | pGIPZ-NR1-1 | 1 μg | 1% formalin | 50 μL |
| B6 | pGIPZ-NR1-1 | 5 μg | 1% formalin | 50 μL |
| B7 | pGIPZ-NR1-1 | 10 μg | 1% formalin | 50 μL |

$^a$injecting 1% formalin on contralateral paw

Figure 4:
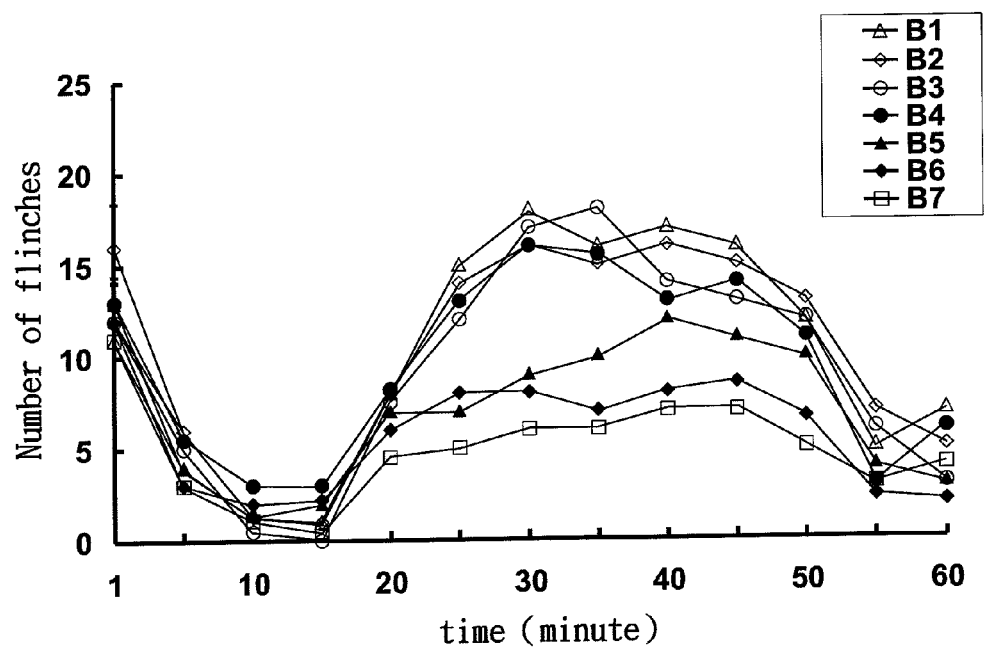
FIG. 4 is a line chart illustrating data of flinch responses in rats on formalin-induced nociception.

Referring to FIG. 4, the formalin-induced flinching responses in the SD rats of the groups (B1) to (B6) are shown. It is noted that the flinching behaviors of rats in the groups (B5) to (B7) are dramatically minor than that of rats in the groups (B1) to (B5), showing a flinch frequency of 4-11 times/per minute in the acute phase. Also, it is observed that the flinch frequency of rats in the groups (B5) to (B7) decreases by the dosage of injected pGIPZ-NR1-1. Additionally, with reference to curve (B5), it is indicated that the pGIPZ-NR1-1 induced antinociception is limited to injected paw, and thus that there is no relief on pain for rats' contralateral paw after formalin injection. It is suggested that, the antinoceciptive effect conducted by the microRNA-based short hairpin RNA of the present invention has a dose-depended manner, and also is localized at where it is treated rather than systemic.

Figure 5:
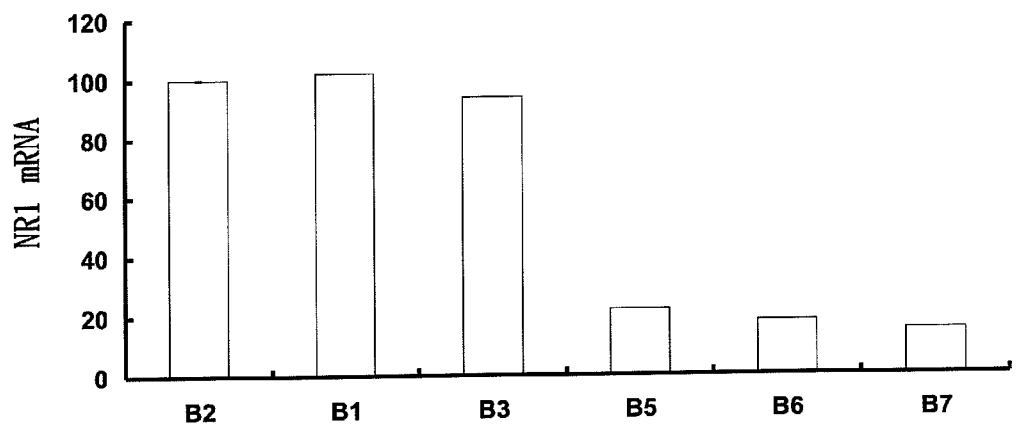
FIG. 5 is a bar chart illustrating protein expression of NR1 in rats after subcutaneous injection of the microRNA-based short hairpin RNA of the present invention.

Referring to FIG. 5, the mRNA expression of NR1 subunit on rats in each group are shown, wherein the NR1 expression is significantly lower in rats of the groups (B5) to (B7) than that of rats in the groups (B1) to (B3). In the present trial, the expressed level of mRNA of NR1 subunit on rats in the group (B2) is defined as 100% and thus that, the SD rats in the groups (B1), (B3), (B5) to (B7) have 102%, 94%, 22%, 18%, and 15% of NR1 expression respectively in comparison with the group (B1). It is indicated that the silencing effects on NR1 subunit induced by the pGIPZ-NR1-1 enhance by the dosage of injected pGIPZ-NR1-1.

It is believed that, the antinociception mediated by the microRNA-based short hairpin RNA of the present invention is localized and perform in a dose-depended manner. Generally, a higher dose of the shRNA of the present invention will lead to stronger silencing effect on the target gene. Accordingly, the microRNA-based short hairpin RNA of the present invention is sufficient to relieve various kinds of pains, such as acute pain, inflammatory pain and secondary pain, by alternately providing different dosages of the said microRNA-based short hairpin RNA to living organisms, preferably with a dosage of 1 to 10 μg, to achieve long-lasting silencing effects on the target gene, as well as antinociceptive response.

Trial of (C) time course:

With reference to Table 3, the SD rats are randomly assigned into eight groups including (C1) to (C8), with subcutaneous injecting 14, PEI or 5 μg pGIPZ-NR1-1 to rats 1, 3, 7, or 14 days prior than the second injection respectively. In the present trial, the groups (C1, C3, C5, and C7) are served as controls. Similar to the trials of (A) microRNA-based short hairpin RNA and (B) dose-effect, the flinching test and the tissue dissection are also carried out on the SD rats of the eight groups after the second injection for timely analyzing rats' pain response and NR1 expression.

TABLE 3

Group Assignment in the Trial of (C) Time Course

| groups | First injection | | | Second injection | |
|---|---|---|---|---|---|
| | agents | time | dose | agents | dose |
| C1 | PEI | 1 days | 1 μL | 1% formalin | 50 μL |
| C2 | pGIPZ-NR1-1 | 1 days | 5 μg | 1% formalin | 50 μL |
| C3 | PEI | 3 days | 1 μL | 1% formalin | 50 μL |
| C4 | pGIPZ-NR1-1 | 3 days | 5 μg | 1% formalin | 50 μL |
| C5 | PEI | 7 days | 1 μL | 1% formalin | 50 μL |
| C6 | pGIPZ-NR1-1 | 7 days | 5 μg | 1% formalin | 50 μL |
| C7 | PEI | 14 days | 1 μL | 1% formalin | 50 μL |
| C8 | pGIPZ-NR1-1 | 14 days | 5 μg | 1% formalin | 50 μL |

Figure 6:
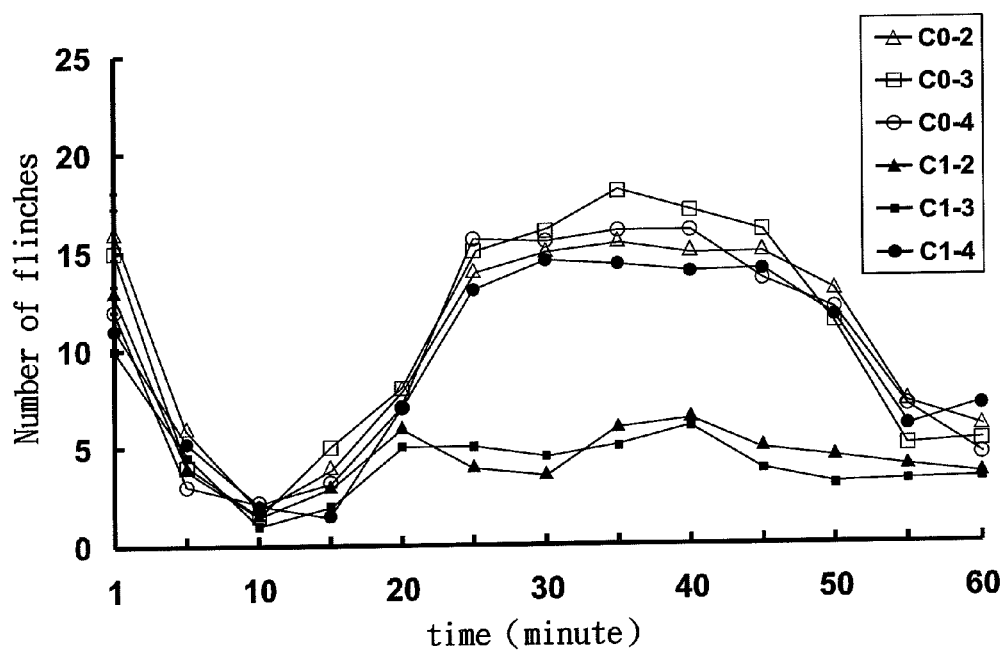
FIG. 6 is a line chart illustrating data of flinch responses in rats on formalin-induced nociception.

Referring to the FIG. 6, the formalin-induced flinching responses in the SD rats of groups (C1) to (C8) are summarized. It is noticed that numbers of flinch on rats of the groups (C4) and (C6) are less than that on rats in the groups (C1) to (C3), (C5) and (C7) to (C8), with only 3-7 times/per minute of flinch in the acute phase. It is suggested that the antinociceptive effect caused by the injected pGIPZ-NR1-1 of the present invention lasts for seven days.

Figure 7:
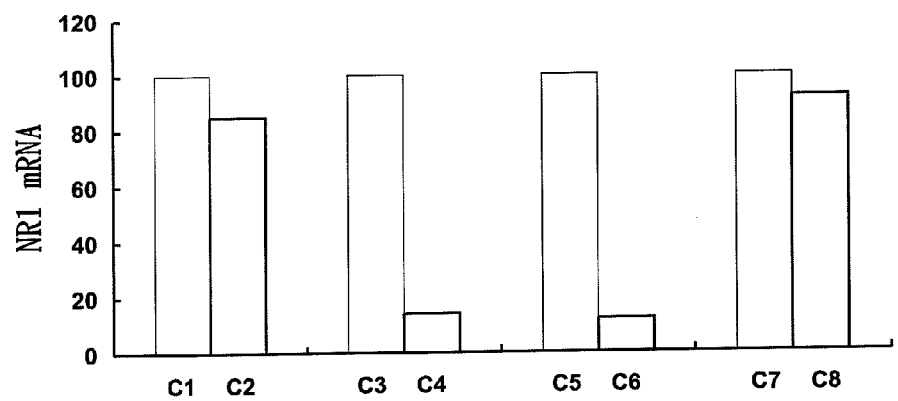
FIG. 7 is a bar chart illustrating mRNA expression of NR1 in rats after subcutaneous injection of the microRNA-based short hairpin RNA of the present invention.
Figure 8:
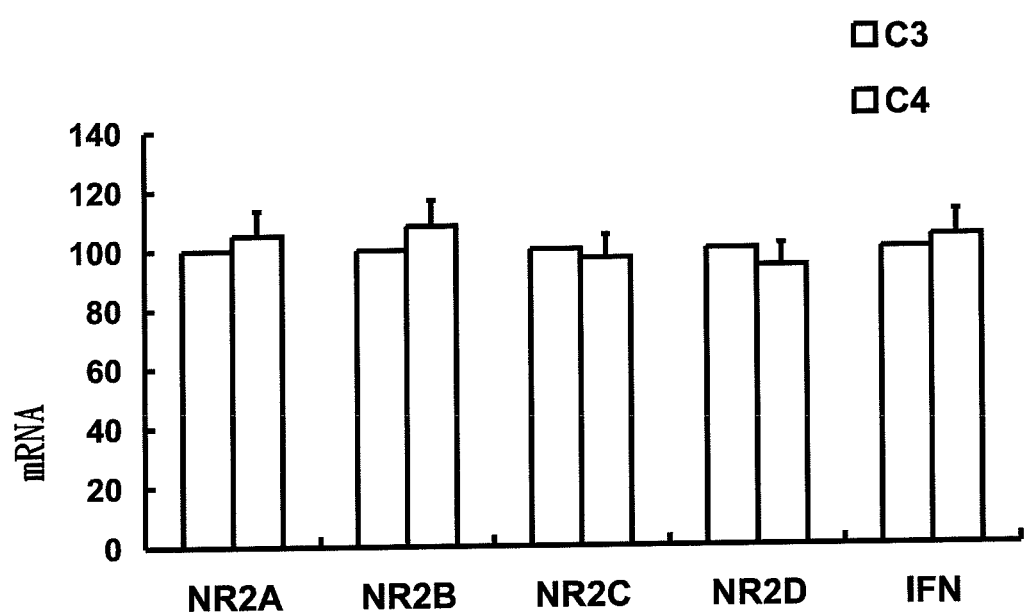
FIG. 8 is a bar chart illustrating mRNA expression of NR1, NR2B, NR2C, NR2D and α-interferon in rats after subcutaneous injection of miRNA.

Referring to FIGS. 7 and 8, the mRNA expressions of NR1 subunit on rats in each group, as well as the mRNA expression of NR2A, NR2B, NR2C, NR2D and α-interferon of rats in the groups (C3) and (C4) are shown. In the present trial, specific primer pairs of NR2A set forth in SEQ ID NO: 10 and 11, NR2B set forth in SEQ ID NO: 12 and 13, NR2C set forth in SEQ ID NO: 14 and 15, NR2D set forth in SEQ ID NO: 16 and 17, and α-interferon set forth in SEQ ID NO: 18 and 19 are further designed and used in the real time PCR program for detecting the mRNA expression of the NR1, NR2A, NR2C, NR2D and α-interferon in the SD rats of the eight groups.

It is indicated that a dramatically decrease in the mRNA expression of NR1 subunit is noted on the third and seventh day after injecting the pGIPZ-NR1-1. Yet, no silencing effect is observed on NR2A, NR2B, NR2C, NR2D and α-interferon. It is believed that, the post-transcriptional gene silence caused by the pGIPZ-NR1-1 of the present invention is specific to the NR1 subunit of NMDA receptor, and therefore, will not interfere with the expression of NR2A, NR2B, NR2C, NR2D and α-interferon.

Figure 9:
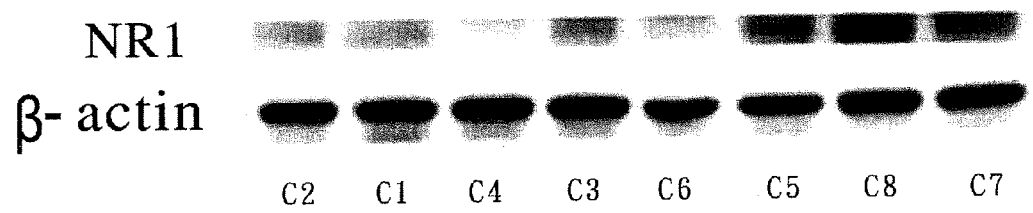
FIG. 9 is a western blot photo showing protein expression of NR1 in rats after subcutaneous injection of the microRNA-based short hairpin RNA of the present invention.

FIG. 9 is a western blot datum, illustrating the protein expression of NR1 in each group. In the present trial, total protein samples of the SD rats in each group are taken from their skin tissues and prepared by 20 times diluting in T-PER tissue protein extraction reagent (PIERCE; Rockford) that contains 25 mM bicine, 150 mM sodium chloride (pH 7.6), protease inhibitors, 100 mM 4-(2-Aminoethyl)benzenesulfonyl fluoride hydrochloride, 80 M aprotinin, crystalline, 5 mM bestatin, 1.5 mM E-64, protease inhibitor, 2M leupeptin and 1 mM pepstatin A. Then, the total protein samples are homogenized with a homogenizer and centrifuged at 12,000 rpm/min for 30 min at 4° C. to collect supernatant. The supernatant are sequentially assayed by a Quant-iT™ protein assay kit (Invitrogen; Carlsbad) and electrophoresed on a 10% sodium dodecylsulfate polyacrylamide gel. Next, the electrophoresed data are transferred to a polyvinylidine fluoride membrane and blocked with 5% nonfat dry milk, ready for the following western blot program. During the western blot, the primary antibody, a 2000 times diluted rabbit polyclonal anti-glutamate receptor NR1 (Sigma; Missouri), and the secondary antibody, a 5000 times diluted horseradish peroxidase-coupled goat anti-rabbit immunoglobulin G (Chemicon; Billerica), are prepared and co-incubated with the polyvinylidine fluoride membrane at a suitable temperature, such as 4° C. or room temperature. Finally, the polyvinylidine fluoride membrane is developed by a western blot chemiluminescence reagent plus (Millipore; Billerica) to obtain the western blot data of FIG. 9. Additionally, for further densitometry the protein analyses, the western blot data are scanned and quantified by an Image-Pro® plus analysis software (MediaCybernetics; Silver Spring) in the present trial.

Figure 10:
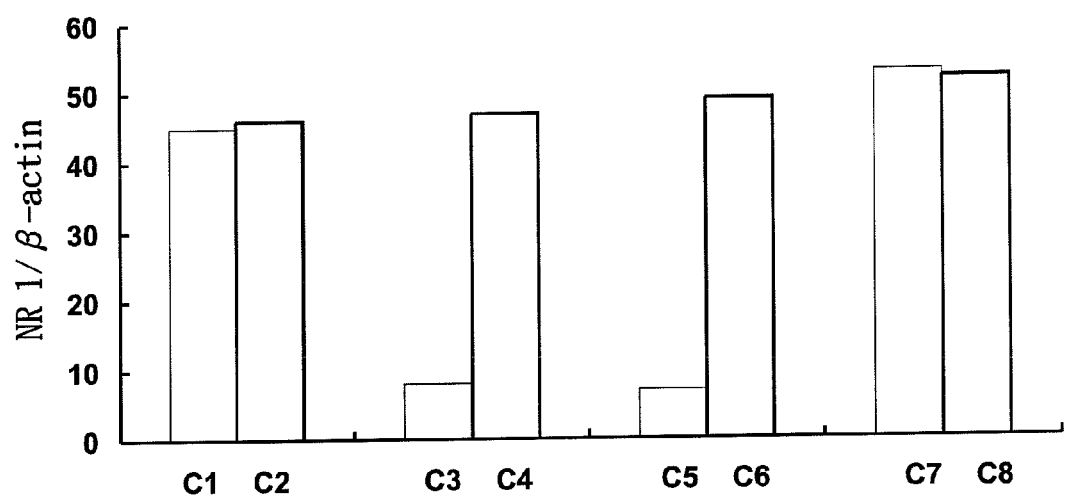
FIG. 10 is a bar chart illustrating ratios of NR1 to β-actin expressed in rats after subcutaneous injection of the microRNA-based short hairpin RNA of the present invention.

With reference to FIG. 9, it is obvious that the protein expressions of the NR1 are significantly lower among other groups. Also, FIG. 10 shows the immunoreactivity ratio between the NR1 and 13-tubulin on the SD rats of the eight groups, wherein the SD rats in the groups (C4) and (C6) only have less than 10% of protein expression, in comparison with the NR1 expression in the group (C1) with around 46-52% in the immunoreactivity ratio between NR1 and β-tubulin. It is further proved that, the post-transcriptional gene silence caused by the pGIPZ-NR1-1 of the present invention lasts for seven days.

In summary, the microRNA-based short hairpin RNA of the present invention specifically target to the NR1 subunit of N-methyl-D-aspartate receptor, leading to fast and long-lasting silencing effect on the NR1 subunit, and achieving long-lasting antinociception in living organism. Generally, antinociception and the silence effect of NR1 subunit mediated by the microRNA-based short hairpin RNA of the present invention will lasts for seven days. Therefore, the microRNA-based short hairpin RNA of the present invention will not cause any permanent disorders to the NR1 subunit of NMDA receptor in the living organism.

Through the present invention, the microRNA-based short hairpin RNA is designed and provided for specifically targeting to NR1 subunit of NMDA receptor, and which is proved to show fast and long-lasting post-transcriptional gene silencing on the NR1 subunit, and result in temporary antinociceptive effect. Furthermore, the silencing effects and antinociception caused by the microRNA-based short hairpin RNA increase by the dose thereof, generally lasts for seven days and refers to no interference on other non-target genes, such as NR2A, NR2B, NR2C, NR2D and α-interferon.

Therefore, an analgesic based on the microRNA-based short hairpin RNA of the present invention, is potential to be developed and applied to clinical medicine for treating pathological pain, and which comprises the microRNA-based short hairpin RNA of the present invention either being artificially synthesized or expressed by the pGIPZ vector, preferably being expressed by the pGIPZ vector, and an pharmaceutics acceptable vehicle. The microRNA-based short hairpin RNA can be pGIPZ-NR1-1, pGIPZ-NR1-2 or a mixture thereof, and the acceptable vehicle can be polyethyleneimine (PEI) or any other acceptable reagents. Preferably, the analgesic comprises the microRNA-based short hairpin RNA in a dose of 1 μg to 10 μg, and delivered to a target organism every seven days via subcutaneous injection. The analgesic can be in the form of a liquid medicine for subcutaneous injection or ointment. Generally, the analgesic can be given to a target organism individually or combined with other acceptable medicaments, for providing sustaining and localized anti-pain effect on patients.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A microRNA-based short hairpin RNA for gene silencing the genetic expression of NR1 subunit of N-methyl-D-aspartate receptor comprising:
a single strand RNA fragment comprising a first fragment, a second fragment and a connecting fragment, wherein the first fragment and the second fragment are complementary to each other, and are spaced and connected by the connecting fragment, with the connecting fragment being randomly arranged nucleotides, with the first fragment having a Drosha recognized cleavage site, a silencing site and a Dicer recognized cleavage site, with the Drosha recognized cleavage site and the Dicer recognized cleavage site being spaced and connected by the silencing site, with the silencing site encoding homologous nucleotides corresponding to NR1 subunit of N-methyl-D-aspartate receptor,
wherein the microRNA-based short hairpin RNA comprises a sequence as set forth in SEQ ID No: 6.

2. The microRNA-based short hairpin RNA as defined in claim 1, wherein the connecting fragment comprises more than 10 nucleotides.

3. A microRNA-based short hairpin RNA for gene silencing the genetic expression of NR1 subunit of N-methyl-D-aspartate receptor comprising:
a single strand RNA fragment comprising a first fragment a second fragment and a connecting fragment, wherein the first fragment and the second fragment are complementary to each other, and are spaced and connected by the connecting fragment, with the connecting fragment being randomly arranged nucleotides, with the first fragment having a Drosha recognized cleavage site, a silencing site and a Dicer recognized cleavage site, with the Drosha recognized cleavage site and the Dicer recognized cleavage site being spaced and connected by the silencing site, with the silencing site encoding homologous nucleotides corresponding to NR1 subunit of N-methyl-D-aspartate receptor, wherein the microRNA-based short hairpin RNA comprises a sequence as set forth in SEQ ID No: 7.

4. An analgesic drug for skin inflammation pain comprising:
a microRNA-based short hairpin RNA as defined in claim 1; and
at least one pharmaceutical acceptable vehicle for the microRNA-based short hairpin RNA.

5. The analgesic drug for skin inflammation pain as defined in claim 4, wherein the at least one pharmaceutical acceptable vehicle is polyethyleneimine.

6. The analgesic drug for skin inflammation pain as defined in claim 4, wherein the microRNA-based short hairpin RNA is encoded by a pGIPZ vector.

7. The analgesic drug for skin inflammation pain as defined in claim 6, wherein the dosage of the microRNA-based short hairpin RNA is 1 μg to 10 μg, being delivered every 7 days.

8. The analgesic drug for skin inflammation pain as defined in claim 6, wherein the ratio of the microRNA-based short hairpin RNA to the at least one acceptable vehicle is 5 μg: 1 μL.

9. The microRNA-based short hairpin RNA as defined in claim 3, wherein the connecting fragment comprises more than 10 nucleotides.

10. An analgesic drug for skin inflammation pain comprising:
a microRNA-based short hairpin RNA as defined in claim 3; and
at least one pharmaceutical acceptable vehicle for the microRNA-based short hairpin RNA.

11. The analgesic drug for skin inflammation pain as defined in claim 10, wherein the at least one pharmaceutical acceptable vehicle is polyethyleneimine.

12. The analgesic drug for skin inflammation pain as defined in claim 10, wherein the microRNA-based short hairpin RNA is encoded by a pGIPZ vector.

13. The analgesic drug for skin inflammation pain as defined in claim 12, wherein the dosage of the microRNA-based short hairpin RNA is 1 μg to 10 μg, being delivered every 7 days.

14. The analgesic drug for skin inflammation pain as defined in claim 12, wherein the ratio of the microRNA-based short hairpin RNA to the at least one acceptable vehicle is 5 μg: 1 μL.

* * * * *